US00PP10301P

United States Patent [19]

Kientzler

[11] Patent Number: Plant 10,301

[45] Date of Patent: Mar. 24, 1998

[54] NEW GUINEA IMPATIENS PLANT NAMED 'MOALA'

[75] Inventor: Ludwig Kientzler, Gensingen, Germany

[73] Assignee: Paul Ecke Ranch, Inc., Encinitas, Calif.

[21] Appl. No.: 781,231

[22] Filed: Jan. 10, 1997

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of New Guinea Impatiens plant named 'Moala', characterized by its flat and rounded dark red-colored flowers; upright and mounded growth habit; and dark green, glossy, non-variegated foliage.

1 Drawing Sheet

The present invention relates to a new and distinct cultivar of New Guinea Impatiens plant, botanically known as *Impatiens hawkeri*, known by the name 'Kiala', and hereinafter referred to b the cultivar name 'Moala'.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of a proprietary seedling selection identified as DR261 as the male, or pollen parent, with the proprietary seedling selection identified as R353 as the female, or seed patent. The cultivar 'Moala' was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of 'Moala'. These characteristics in combination distinguish 'Moala' as a new and distinct cultivar:

1. Flat and rounded dark red-colored flowers.
2. Upright and mounded growth habit.
3. Dark green, glossy, non-variegated foliage.

The new New Guinea Impatiens is similar in flower color to the New Guinea Impatiens cultivar 'Deep Red' (disclosed in U.S. Plant Pat. No. 9,521). However in side-by-side comparisons in Encinitas, Calif., under commercial practice, plants of the new New Guinea Impatiens differed from plants of the cultivar 'Deep Red' in the following characteristics:

1. Plants of the new New Guinea Impatiens are less upright and more mounded than plants of the cultivar 'Deep Red'.
2. Plants of the new New Guinea Impatiens are more freely branching and denser than plants of the cultivar 'Deep Red'.
3. Leaves of plants of the new New Guinea Impatiens have redder veins than leaves of plants of the cultivar 'Deep Red'.
4. Leaves of plants of the new New Guinea Impatiens have shorter petioles than leaves of plants of the cultivar 'Deep Red'.
5. Flowers of plants of the new New Guinea Impatiens are larger and thicker than flowers of plants of the cultivar 'Deep Red'.

6. Peduncles of plants of the new New Guinea Impatiens are longer, stronger and more red than peduncles of plants of the cultivar 'Deep Red'.

A detailed comparison of plants of the new New Guinea Impatiens and the cultivar 'Deep Red' appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical plant of 'Moala'.

The second photograph comprises a close-up view of typical flowers and upper (left) and lower (right) surfaces of leaves of the cultivars 'Deep Red' (top of photo) and 'Moala' (bottom of photo).

The flower and foliage colors in the photographs may differ from the actual colors due to light reflectance.

The cultivar 'Moala' has not been observed under all possible environmental conditions. The phenotype may vary somewhat with variations in environment such as temperature and light intensity, without, however, any variance in genotype. The following observations, measurements and comparisons describe plants grown 10-cm pots in Encinitas, Calif., under commercial practice in a fiberglass-covered greenhouse with day temperatures ranging from 23 to 29C. and night temperatures ranging from 16 to 18C. and about 3,000 footcandles.

In the following description, color references are made to The Royal Horticultural Society Colour Chart except where general terms of ordinary dictionary significance are used.

Classification:

*Botanical.*—*Impatiens hawkeri* 'Moala'.

*Commercial.*—New Guinea Impatiens cv. 'Moala'.

Parentage:

*Male parent.*—Proprietary seedling selection DR261.

*Female parent.*—Proprietary seedling selection R353.

Propagation:

*Type cutting.*—Terminal cuttings.

*Time to initiate roots.*—About 15 days with 21C soil temperature.

Plant description:

*Plant form.*—Upright and mounded.

*Growth habit.*—Moderately vigorous. Moderate branching. Suitable for 10 to 25-cm containers.

*Plant size.*—Height: About 16 cm. Width or spread: About 26 cm.

*Lateral branches.*—Quantity: About seven. Size: Length: About 11 cm. Diameter: About 8 mm. Internode length: About 4 cm. Color: 146A with prominent 59A streaks.

*Foliage description.*—Leaves simple, generally symmetrical, abundant, opposite or in whorls of three, horizontal to plant and flat in aspect. Size, largest leaves: Length: About 10.5 cm. Width: About 5 cm. Shape: Ovate with acuminate apex, attenuate base and ciliate margin. Texture: Smooth, glossy. Color: Young foliage, upper surface: Greener than 146A. Young foliage, lower surface: 146B. Fully expanded foliage, upper surface: 147A. Fully expanded foliage, lower surface: 147B. Venation, upper surface: 59A. Venation, lower surface: 59A. Petiole: Size: Length: About 3.5 cm. Diameter: About 3.5 mm. Color: 59A.

Flower description:

*Flower type and habit.*—Dark red flowers. Freely and continuously flowering. Flowers arise from leaf axils. Usually eight flowers per lateral branch. Flowers positioned above the foliage and face upward or outward. Flowers flat and rounded. Flowers persistent.

*Flowering season.*—Year-round under greenhouse conditions. In the garden, flowering is continuous from spring until fall.

*Flower size.*—Length: About 7 cm. Width: About 7 cm. Depth: About 4 mn.

*Flower buds.*—Size: Length: About 1.8 cm. Diameter: About 1 cm. Shape: Ovoid. Color: 46A.

*Petals.*—Quantity: Five. Size (largest petals): Length: Top petal: About 3 cm. Middle petals: About 3.25 cm. Bottom petals: About 4.25 cm. Width: Top petal: About 5 cm. Middle petals: About 3.5 cm. Bottom petals: About 3.5 cm. Shape: Cordate with emarginate apex, cuneate or obtuse base and entire margin. Texture: Velvety, smooth. Color: When opening, upper surface: Iridescent, darker red than 45A. When opening, lower surface: Iridescent, 45C. Fully opened, upper surface: Iridescent, darker red than 45A. Fully opened, lower surface: Iridescent, 45C. Fading to: Color does not fade.

*Spur.*—Length: About 5.5 cm. Shape: Narrow and curved. Color: Proximal: 60A, Distal: 59A.

*Peduncles.*—Length: About 5 cm. Angle: Erect and outward, Strength: Strong. Color: 59A.

*Reproductive organs.*—Androecium: Stamen number: Five, anthers fused, filaments free. Anther shape: Obovate. Anther size: 6 by 4 mm. Anther color: Light yellow with red, 45A, base. Amount of pollen: Moderate. Pollen color: Cream. Gynoecium: Five-loculate fused. Gynoecium color: 144A to darker than 59A.

Disease resistance: Under commercial conditions, resistance nor susceptibility to pathogens has not been observed.

Seed development: Seed production is not usually observed.

CHART A

| CHARACTERISTIC | 'MOALA' | 'DEEP RED' |
|---|---|---|
| GROWTH HABIT | Upright, mounded | Upright, open |
| NUMBER OF LATERAL BRANCHES | About 7 | About 5 |
| STEM COLOR | 146A with prominent 59A streaks | 144A |
| LEAF VENATION COLOR, UPPER SURFACE | 59A | Light green with 59B tinge |
| LEAF VENATION COLOR, LOWER SURFACE | 59A | Light green with 59B tinge |
| PETIOLE LENGTH | About 3.5 cm | About 4.5 cm |
| PETIOLE COLOR | 59A | Light green with streaks of 59B |
| FLOWER DIAMETER | About 7 cm | About 6 cm |
| FLOWER DEPTH | About 4 mm | About 3 mm |
| PEDUNCLE LENGTH | About 5 cm | About 4.25 cm |
| PEDUNCLE STRENGTH | Strong | Moderate |
| PEDUNCLE COLOR | 59A | 144A with 58A streaks |

It is claimed:

1. A new and distinct cultivar of New Guinea Impatiens plant named 'Moala', as illustrated and described.

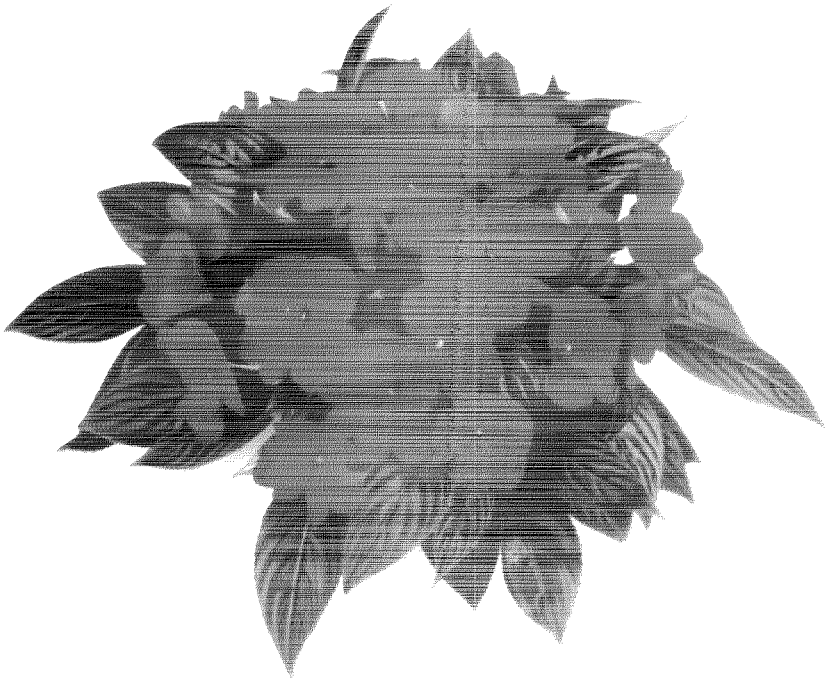
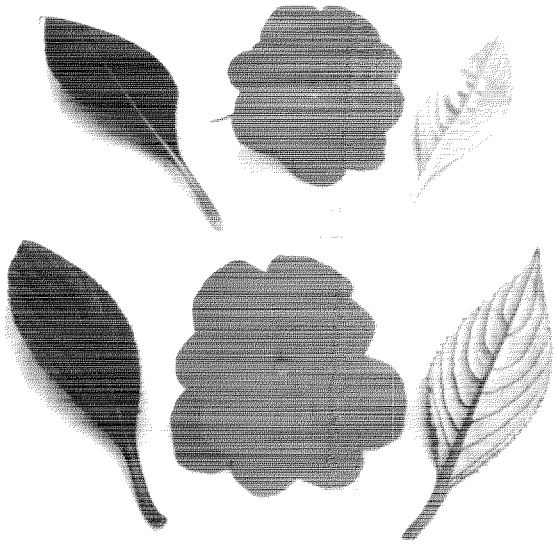

* * * * *